United States Patent

Fujikawa et al.

Patent Number: 4,841,068
Date of Patent: Jun. 20, 1989

[54] 3-HYDROXY PYRAZOLE DERIVATIVES

[75] Inventors: Yoshihiro Fujikawa, Chiba; Masazumi Wakamatsu, Yamaguchi; Mariko Fukui, Tokyo; Tadashi Miyasaka, Kanagawa, all of Japan

[73] Assignee: Nissan Chemical Industries, Ltd., Tokyo, Japan

[21] Appl. No.: 16,618

[22] Filed: Feb. 19, 1987

[30] Foreign Application Priority Data

Feb. 19, 1986 [JP] Japan .................. 61-34320

[51] Int. Cl.$^4$ ........................... C07D 231/46
[52] U.S. Cl. ..................... 548/365; 544/262
[58] Field of Search ........................... 548/365

[56] References Cited

FOREIGN PATENT DOCUMENTS 0157415 10/1985 European Pat. Off. ............ 544/262

OTHER PUBLICATIONS

Chem. Pharm. Bull., 31(4)12228–1234 (1963), Synthesis of 2-Substituted 2,6-Dihydro-3-hydroxy-7-H-pyrazolo [4,3-d]pyrimidin-7-ones, Ochi et al.
Albert, "Annelation of a Pyrimidine Ring to an Existing Ring", *Advances in Heterocyclic Chemistry*, 32, pp. 43–46 and 60–61 (1982).
Albert, "v-Triazolo[4,5-d]pyrimidines (8-Azapurines), Part X, New Routes to v-Triazolo . . . Carbonitriles", J. C. S. Perkin I, pp. 461–471 (1972).

*Primary Examiner*—Robert W. Ramsuer
*Attorney, Agent, or Firm*—Sughrue, Mion, Zinn, Macpeak & Seas

[57] ABSTRACT

Disclosed is a process for preparing a 3-hydroxy-7-mercaptopyrazolo[4,3-d]pyrimidine compound represented by the general formula (IX):

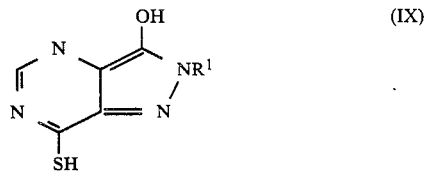

wherein
$R^1$ is a hydrogen atom, an alkyl group having 1 to 4 carbon atoms, a phenyl group or a substituted phenyl group, which comprises:
from a pyrazole compound represented by the general formula (III):

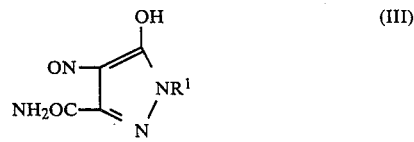

wherein $R^1$ is the same as defined above.
Also disclosed are pyrazole compounds represented by the general formula (I):

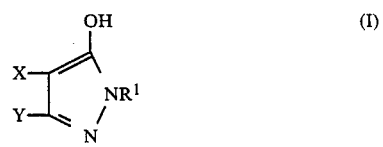

The compounds serve as intermediate for preparing the compound of the formula (IX).

13 Claims, No Drawings

3-HYDROXY PYRAZOLE DERIVATIVES

BACKGROUND OF THE INVENTION

The present invention relates to a process for preparing 3-hydroxy-7-mercapto-pyrazolo[4,3-d]pyrimidines (which are useful as a starting material for preparation of pyrazolo[4,3-d]pyrimidine derivatives useful as an antihyperlipidemic agent as described hereinafter) from 3-hydroxy-4-nitroso-5-alkoxycarbonyl-pyrazole through a novel compound, 3-hydroxy-4-dialkylaminomethyleneamino-5-cyanopyrazole, and also to the novel intermediate compounds.

As described in European Patent Application No. 0157415 publised on Oct. 9, 1985, 3-hydroxy-7-mercaptopyrazolo[4,3-d]pyrimidine is useful as an intermediate product for the preparation of anti-hyperlipidemic agents. Heretofore, 3-hydroxy-7-mercaptopyrozolo[4,3-d]pyrimidines (IX) have been prepared according to the following Reaction Scheme 1.

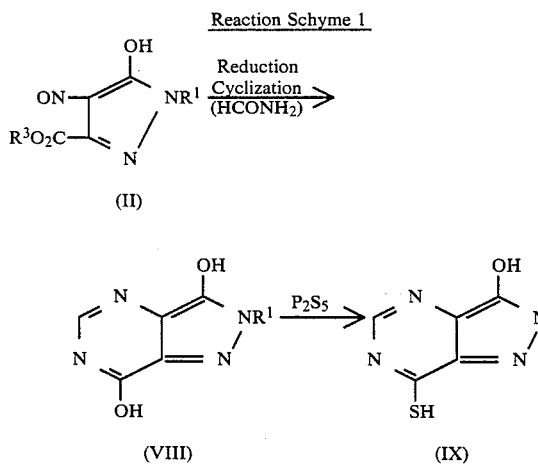

In the above formulae, $R^1$ is a hydrogen atom, a lower alkyl group having 1 to 4 carbon atoms, a phenyl group or a substituted phenyl group substituted with an alkyl group having 1 to 4 carbon atoms or an alkyloxy group having 1 to 4 carbon atoms, and $R^3$ is an alkyl group having 1 to 4 carbon atoms.

As shown in the Reaction Scheme 1, 3-hydroxy-4-nitroso-5-alkoxycarbonylpyrazole (II) is reduced and then cyclized in formamide by heating at elevated temperature to once form 3,7-dihydroxy-pyrazolo[4,3-d]pyrimidine (VIII) and, thereafter, this 3,7-dihydroxy-pyrazolo[4,3-d]pyrimidine (VIII) is heated in pyridine along with diphosphorus pentasulfide.

The above process has disadvantages in that heating at temperatures as high as more than 150° C. is needed in the cyclization reaction to form 3,7-dihydroxy-pyrazolo [4,3-d]pyrimidine (VIII); the reaction between 3,7-dihydroxypyrazolo[4,3-d]pyrimidine (VIII) and diphosphorus pentasulfide is difficult to control and its yield is low; and in that the purity of the formed 3-hydroxy-7-mercaptopyrazolo[4,3-d]pyrimidine (IX) is low.

SUMMARY OF THE INVENTION

An object of the present invention is to provide novel processes for synthesizing 3-hydroxy-7-mercaptopyrazolo[4,3-d]pyrimidines.

Another object of the present invention is to provide novel intermediates for use in the preparation of 3-hydroxy-7-mercaptopyrazolo[4,3-d]pyrimidines and processes for preparing the intermediates.

As a result of extensive research on the preparation of 3-hydroxy-7-mercaptopyrazolo[4,3-d]pyrimidine, it has now been discovered that a novel synthesis process without involving synthesis and modification of 3,7-dihydroxypyrazolo[4,3-d]pyrimidines (VIII) is free from the drawbacks of the conventional process. The present invention is based on the discovery.

Thus, the present invention provides a pyrozole compound represented by the general formula (I):

wherein:

$R^1$ is a hydrogen atom, an alkyl group having 1 to 4 carbon atoms, a phenyl group or a substituted phenyl group substituted with an alkyl group having 1 to 4 carbon atoms or an alkyloxy group having 1 to 4 carbon atoms;

X is a nitroso group, an amino group or $(R^2)_2NCH=N-$ (wherein $R^2$ is an alkyl group having 1 to 3 carbon atoms); and Y is $-C(O)NH_2$ when $R^1$ is an alkyl group having 1 to 4 carbon atoms, a phenyl group or a substituted phenyl group and X is a nitroso group, or $-C(O)NH_2$ when $R^1$ is a hydrogen atom, an alkyl group having 1 to 4 carbon atoms, a phenyl group or a substituted phenyl group and X is an amino group, or CN or $-C(S)NH_2$ when $R^1$ is a hydrogen atom, an alkyl group having 1 to 4 carbon atoms, a phenyl group or a substituted phenyl group and X is $(R^2)_2NCH=N-$ (wherein $R^2$ is the same as defined above).

Further, the present invention provides the following processes:

(1) A process for preparing a pyrazole compound represented by the general formula (III):

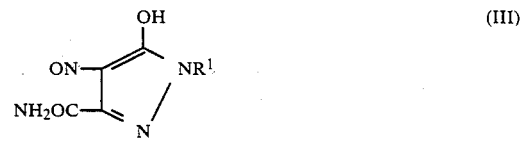

wherein $R^1$ is the same as defined above, which comprises reacting a pyrazole compound represented by the general formula (II):

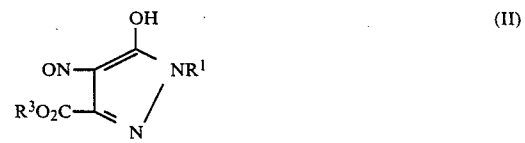

wherein $R^1$ is the same as defined above, and $R^3$ is an alkyl group having 1 to 4 carbon atoms, with ammonia under atmospheric pressure.

(2) A process for preparing a pyrazole compound represented by the general formula (IV):

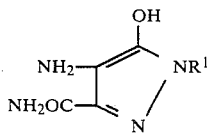 (IV)

wherein R¹ is the same as defined above, which comprises reducing a pyrazole compound represented by the general formula (III):

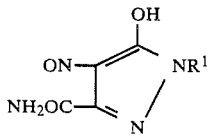 (III)

wherein R¹ is the same as defined above.

(3) A process for preparing a pyrazole compound represented by the general formula (VI):

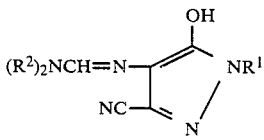 (VI)

wherein R¹ and R² are the same as defined above, which comprises reacting a pyrazole compound represented by the general formula (IV):

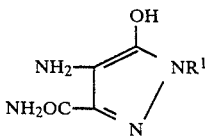 (IV)

wherein R¹ is the same as defined above, with a mixture of dialkylformamide represented by the general formula (V):

wherein R² is the same as defined above, and phosphorus oxychloride, thionyl chloride or phosgene.

(4) A process for preparing a compound represented by the general formula (VII):

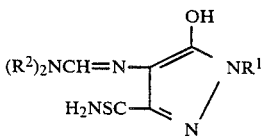 (VII)

wherein R¹ and R² are the same as defined above, which comprises reacting a pyrazole compound represented by the general formula (VI):

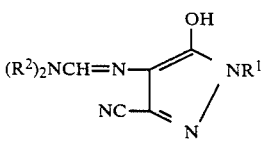 (VI)

wherein R¹ and R² are the same as defined above, with hydrogen sulfide in the presence of a base or with an alkali metal hydrosulfide.

(5) A process for preparing a compound represented by the general formula (IX):

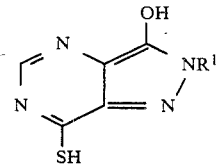 (IX)

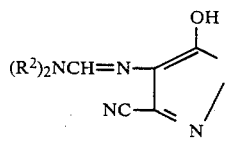 (VI)

wherein R¹ is the same as defined above, which comprises reacting a pyrazole compound represented by the general formula (VI):

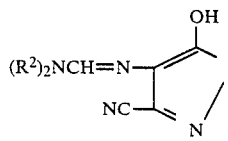 (VI)

wherein R¹ and R² are the same as defined above, with hydrogen sulfide or an alkali metal hydrosulfide in the presence of a base and, thereafter, cyclizing.

(6) A process for preparing a compound represented by the general formula (IX):

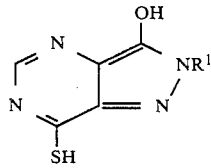 (IX)

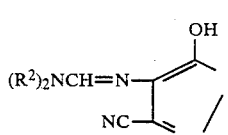 (VI)

wherein R¹ is the same as defined above, which comprises cyclizing a pyrazole compound represented by the general formula (VII):

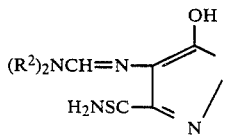 (VII)

wherein R¹ and R² are the same as defined above, by heating.

(7) A process for preparing a compound represented by the general formula (IX):

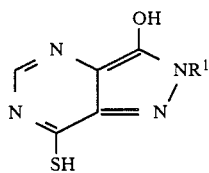

(IX)

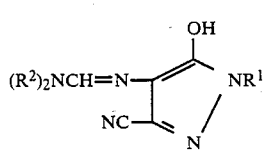

(VI)

wherein R¹ is the same as defined above, which comprises:
reducing a pyrazole compound represented by the general formula (III):

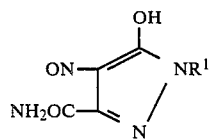

(III)

wherein R¹ is the same as defined above, to form a pyrazole compound represented by the general formula (IV):

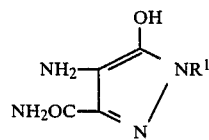

(IV)

wherein R¹ is the same as defined above;
without isolation of the compound represented by the general formula (IV), reacting the compound represented by the general formula (IV) with a mixture of a dialkylformamide represented by the general formula (V):

(R²)₂NC(O)H wherein R² is the same as defined above and phosphorus oxychloride, thionyl chloride or phosgene to form a pyrazole compound represented by the general formula (VI):

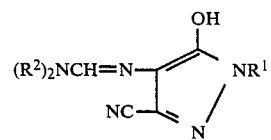

(VI)

wherein R¹ and R² are the same as defined above;
without isolation of the compound represented by the general formula (VI), reacting the compound represented by the general formula (VI) with hydrogen sulfide in the presence of a base or with an alkali metal hydrosulfide to form a compound represented by the general formula (VII):

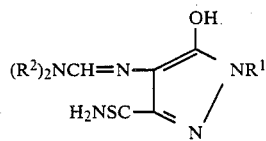

(VII)

wherein R¹ and R² are the same as defined above; and
without isolation of the compound represented by the general formula (VII), cyclizing the compound represented by the general formula (VII) to form the desired compound.

DETAILED DESCRIPTION OF THE INVENTION

The term "room temperature" used herein refers to a temperature of 10° to 30° C.

The term "low temperature" or "a low temperature" used herein refers to temperatures or a temperature of 0° to 40° C.

The above novel synthesis process relates to a series of reactions including the steps A to D as illustrated in Reaction Scheme 2 as shown below.

Reaction Scheme 2

-continued
Reaction Scheme 2

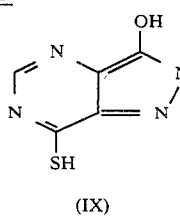

(IX)

In the above formulae, $R^1$ is a hydrogen atom, a lower alkyl group having 1 to 4 carbon atoms, a phenyl group or a substituted phenyl group substituted with an alkyl group having 1 to 4 carbon atoms or an alkyloxy group having 1 to 4 carbon atoms, $R^2$ is an alkyl group havig 1 to 3 carbon atoms and $R^3$ is an alkyl group having 1 to 4 carbon atoms.

The step A is directed to the conversion of the alkoxycarbonyl group into the carbamoyl group. This has heretofore been conducted by heating in a sealed tube along with ammonia water (see Chem. Pharm. Bull., 31, 1288 (1983)). In accordance with the present invention, it has been found that the reaction proceeds rapidly and quantitatively by stirring in a more simplified manner, i.e., stirring at room temperature in an excess of ammonia water, usually 2 to 5 times by mole of ammonia water per mol of the compound (II) so that the amidation is achieved completely.

The step B is a step where a plurality of reactions are carried out without isolation of intermediate products.

In the first place, the nitroso group of the compound (III) is reduced in only a dialkylformamide (e.g., dimethylformamide, diethylformamide, dipropylformamide or diisopropylformamide, particularly dimethylformamide) or in a mixed solvent composed of a dialkylformamide (e.g., dimethylformamide, diethylformamide, dipropylformamide or diisopropylformamide, particularly dimethylformamide) and benzene, toluene, acetonitrile, ether, hexane or the like. In this case, the dialkylformamide acts as a reaction reagent and also as a dissolving agent. Thus it can be used in an amount of 2 mols or more per mol of the compounds (III) or more excessively. When it is used alone as a solvent, it is used in such an amount that the weight ratio of the dialkylformamide to the compound (III) is 4:1 to 8:1 and preferably 5:1 to 6:1. If the dialkylformamide is used in a large amount, the crystals of the compound (VI) are dissolved in the solvent and the precipitation amount is decreased.

The above reduction reaction can be carried out with ease in a hydrogen atmosphere in the presence of a catalyst such as palladium-carbon. The amino pyrazole formed is oxidized rapidly in the air, forming an unknown blue-violet colored substance. Thus, without isolation, it is sent to the subsequent reaction step in the form of a solution.

At the end of the reaction, the solution is cooled with ice, and phosphorus oxychloride, or a mixture (1:1 by mol) of phosphorus oxychloride, thionyl chloride or phosgene and a dialkylformamide (e.g., dimethylformamide, diethylformamide, dipropylformamide or diisopropylformamide, particularly dimethylformamide) is added portionwise in an amount of 2 mols or more, preferably 2.1 to 2.5 mols per mol of the compound (III), and the reaction is further completed while cooling with ice or at room temperature.

At this time, the formation of a cyano group due to the dehydration reaction of the carbamoyl group and the protection of the amino group by the dialkylaminomethylene group proceed simultaneously. Upon hydrolysis by addition of a small amount of water, the compound (VI) is obtained in a crystal form in a high yield.

The steps C and D are directed to the cyclization through the addition of $H_2S$. This can be carried out under various conditions. Hydrogen sulfide gas is bubbled in a solution or suspension of the compound (VI) under basic conditions to such an extent that the solution becomes acidic and the reaction is completed, thereby forming a hydrosulfide compound. Then, by stirring for at least 1 hour, preferably 1 to 2 hours while heating at 40° to 80° C. or for a long time, such as more than 2 hours, preferably more than 10 hours at room temperature, the cyclization is completed. Even when the compound (IV) is added after introduction of hydrogen sulfide, the reaction proceeds similarly.

Bases which can be used include sodium hydroxide, potassium hydroxide, ammonia, alkali metal alcoholates such as sodium methoxide, sodium ethoxide and sodium propoxide, and tertiary amines such as pyridine, triethylamine and triethanolamine.

In a case where such bases as sodium hydroxide and sodium ethoxide are used, if the bases used in such an excess amount such as 5 to 10 mols per mol of the compound (VI), a good yield can be obtained. In the case of tertiary amines, it is used in an amount of 1 to 3 mols, preferably 1 to 1.5 mols per mol of the compound (VI).

As the solvent, water as well as alcohol solvents such as methanol, ethanol, propanol and butanol, can be used. In place of bubbling hydrogen sulfide, it is possible that sodium hydrosulfide or potassium hydrosulfide commercially available as a reagent is used in an amount of 5 to 10 mols per mol of the compound (VI).

In the above reaction, as an intermediate product, the compound (VII) is first formed. This can be confirmed and isolated by thin layer chromatography. However, it is usually unnecessary to isolate it, and the desired product of the cyclization reaction by heating can be easily obtained.

More conveniently, the above-described steps C and D can be carried out continuously subsequently to the preceding steps B₁ and B₂, and it is not necessary for the compound (VI) to be isolated (Compound (VI) is not easy to be isolated in a high yield).

That is, in the step B, after the reaction with the Vilsmeier reagent is completed, water is added portionwise and the catalyst is removed by filtration.

A concentrated aqueous solution of sodium hydroxide, potassium hydroxide or the like is added portionwise to the filtrate while cooling to make the solution alkaline. Thereafter, in the same manner as in the steps C and D, treatment such as introduction of hydrogen sulfide gas and heating is applied, whereupon the compound (IX) can be obtained in nearly the same yield as in the case where the compound (VI) was isolated.

In accordance with the process of the present invention, 3-hydroxy-7-mercaptopyrazolo[4,3-d]pyrimidine (IX) which is an intermediate product for the preparation of compounds useful as an anti-hyperlipdemic agent can be obtained in a simplified manner and in a higher total yield not through 3,7-dihydroxypyrazolo[4,3-d]pyrimidine which is difficult to handle.

The purity of the compound (IX) as obtained by the process of the present invention is markedly much higher than that as obtained by the conventional methods, and thus the compound (IX) as obtained by the process of the present invention does not almost need purification.

In addition, the present invention provides a novel and useful intermediate product for use in the process of the present invention.

It is believed that 3-hydroxypyrazoles can take a tautomeric structure. For example, among the above 3-hydroxypyrazoles, the compound (III) can take a tautomeric structure of the pyrazolone type:

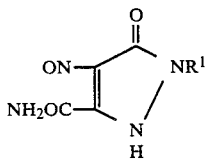

(Pyrazolone type of the compound (III). The compound (IX) can take a tautometric structure of the 3-hydroxy-pyrazolo[4,3-d]pyrimidine-7-thione type:

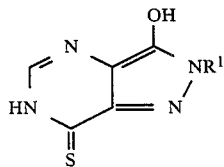

(Thione type of the compound (IX)).

For the sake of simplification, only the hydroxy type and the mercapto type structures are employed in the present specification.

Of the above compounds (I), those in which $R^1$ is a methyl group, an ethyl group or a phenyl group, X is a nitroso group or $(CH_3)_2NCH=N-$, Y is $CONH_2$ when X is a nitroso group of $-CN$ or $-C(S)NH_2$ when X is $(CH_3)_2NCH=N-$ are preferred, with the compound of formula (I) in which $R^1$ is a methyl group, X is $(CH_3)_2N-CH=N-$ and Y is CN being particularly preferred.

The present invention is described in greater detail with reference to the following examples, although the present invention is not limited thereto.

EXAMPLE 1

Preparation of 2-methyl-3-hydroxy-4-nitroso-5-carbamoylpyrazole (IIIa) (Compound of the General Formula (III) wherein $R^1$ is a methyl group)

10 g of 2-methyl-3-hydroxy-4-nitroso-5-ethoxycarbonylpyrazole (IIa) ($R^1=CH_3$) and 50 ml of 28% ammonia water were placed in a 100-milliliter flask and stirred at room temperature for 3 hours. The ammonia was distilled away at room temperature and under reduced pressure. 1:1 Hydrochloric acid was added to make the solution acidic, and yellow crystals which precipitated were separated by filtration and washed with water.

Yield: 96%.
M.P.: 220°–225° C. (decomposition).
pmr Spectrum (d$_6$-DMSO) δppm; [3.30(s):3.35(s)=2:3, 3H], [7.43(br.s):8.40(br.s)=2.3, 3H].
MS(m/e): 170 (M+).

EXAMPLE 2

Preparation of 2-ethyl-3-hydroxy-4-nitroso-5-carbamoylpyrazole (IIIb) (Compound of the General Formula (III) wherein $R^1$ is an Ethyl Group)

The above compound was prepared from 2-ethyl-3-hydroxy-4-nitroso-5-ethoxycarbonyl-pyrazole (IIb) ($R^1=C_2H_5$) in the same manner as in Example 1.
Yield: 61%.
M.P.: 178.0°–179.5° C.
pmr Spectrum (CDCl$_3$) δppm; 1.36(t, 3H, J=7.2Hz), 1.61(br.s, 2H), 3.92(q, 2H, J=7.2Hz).

EXAMPLE 3

Preparation of 2-methyl-3-hydroxy-4-dimethylaminomethyleneamino-5-cyano-pyrazole (VIa) (Compound of the General Formula (VI) wherein $R^1$ and $R^2$ are both Methyl Groups)

20 g (0.118 mol) of the compound (IIIa) and 60 ml of dimethylformamide were placed in a 200-milliliter flask and stirred. After the atmosphere in the flask was replaced with nitrogen, 1 g of 5% palladium-carbon was added, and hydrogen reduction was performed in a hydrogen atmosphere at room temperature and atmospheric pressure. After the completion of the reduction, a solution of 29.4 ml (2.5 time mol equivalent relative to the compound (IIIa)) of phosphorus oxychloride in 30 ml of dimethylformamide was gradually added while cooling with ice. The resulting mixture was further stirred for 30 minutes while cooling with ice and then for 15 hours at room temperature. Then, 5 ml of water was gradually added while cooling with ice to decompose an excess of phosphorus oxychloride. After about 1 hour, 20 ml of methanol was added, and the palladium-carbon was filtered off. The methanol was distilled away at 20°–40° C. and then residual solution was stored for 2 days in a refrigerator. Precipitated crystals were filtered off and washed with acetone to obtain 19.9 g of the desired compound (VIa) (yield: 87.2%).
M.P.: 220°–225° C. (decomposition).
pmr Spectrum (d$_6$-DMSO)
δppm 3.20(6H, s), 3.62(3H, s), 8.26(1H, s).
MS(m/e); 193 (M+).

EXAMPLE 4

Preparation of 2-ethyl-3-hydroxy-4-(dimethylaminomethyleneamino)-5-cyano-pyrazolone (VIb) (Compound of the General Formula (VI) wherein $R^1$ is an ethyl group and $R^2$ is a methyl group)

The above compound (0.31 g) was prepared from 0.5 g of the compound (IIIb) in the same manner as in Example 3.
Yield: 54%
M.P.: 195°–205° C. (decomposition)
pmr Spectrum (d$_6$-DMSO) δppm 1.30(t, 3H, J=7.2Hz), 3.20(s, 3H), 3.27(s, 3H), 4.02(q, 2H, J=7.2Hz), 8.37(s, 1H).
MS(m/e); 207 (M+), 163 (M+-Me$_2$N)

EXAMPLE 5

Preparation of
2-methyl-3-hydroxy-7-mercapto-pyrazolo[4,3-d]pyrimidine (IXa) (Compound of the General Formula (IX) wherein $R^1$ is a Methyl Group)

Preparation Example 1

20 ml of ethanol and 0.91 g (7.6 time mole equivalent relative to the compound (VIa) of metallic sodium were placed in a 50-milliliter flask, and the metallic sodium was dissolved in ethanol by heating. The temperature was decreased to room temperature, and a suspension of 1 g (5.18 mmol) of the compound (VIa) in 5 ml of ethanol was added. In this suspension was bubbled hydrogen sulfide gas at room temperature for 5 hours, and the suspension was then heated at 80° C. for 1.5 hours. Then the temperature was decreased to room temperature, and insoluble yellow solids were removed by filtration. The solids were dissolved in 6 ml of water and a small amount of insoluble material was removed by filtration. To the filtrate was added concentrated hydrochloric acid to make it acidic, and the compound (IXa) which precipitated was filtered, washed with water and dried. 0.71 g (yield: 75.3%)

M.P.: above 320° C.

pmr Spectrum ($d_6$-DMSO) $\delta$ppm 3.71(s, 3H), 7.80(s, 1H).

MS(m/e); 182 (M+).

Preparation Example 2

1.57 g (7.6 time gram equivalent relative to the compound (VIa)) of caustic soda was dissolved in 6 ml of water in a 50-milliliter flask, and hydrogen sulfide gas was bubbled therein at room temperature for 5 hours. Then, 1 g of the compound (VIa) was added and dissolved therein, and hydrogen sulfide was bubbled therein at room temperature for additional 30 minutes. After it was confirmed by thin layer chromatography that the starting material, compound (VIa), disappeared and the thioamide (VIIa) was formed, the mixture was heated for 1.5 hours at 60° C. while bubbling hydrogen sulfide gas. The temperature was decreased to room temperature, and concentrated hydrochloric acid was added to make the solution acidic. Yellow solids which precipitated were filtered off. These solids were dissolved in 9 ml of an aqueous sodium bicarbonate solution, and a small amount of insoluble material was filtered off. The filtrate was rendered acidic by adding concentrated hydrochloric acid. Solids which precipitated were separated by filtration, washed with water and dried to obtain 0.73 g of the compound (IXa) (yield, 77.4%).

Preparation Example 3

(Direct Preparation from Compound (IIIa) without Isolation of Compound (VIa))

1 g of the Compound (IIIa) and 4 ml of dimethylformamide were placed in a 50-milliliter flask and stirred, and after replacing the atmosphere in the flask with nitrogen, 0.05 g of palladlium-carbon was added. After hydrogen reduction at room temperature and atmospheric pressure, 1.47 ml (2.5 time mol equivalent relative to the compound (IIIa)) of phosphorus oxychloride was gradually added while cooling with ice, and the resulting mixture was stirred for 30 minutes. The mixture was stirred at room temperature for 14 hours, and 4 ml of water was gradually added while cooling with ice to decompose an excess of phosphorus oxychloride. After the separation of the palladium-carbon by filtration, a concentrated aqueous solution of caustic soda (a solution prepared by dissolving 4.8 g of caustic soda in 8 ml of water) was added to the filtrate while cooling with ice. Hydrogen sulfide gas was bubbled in the solution for 5 hours at room temperature. The mixture was heated at 60° C. for 1 hour. After the temperature was decreased to room temperature, 1:1 hydrochloric acid was added to make the solution acidic. Yellow solids which precipitated were treated in the same manner as in Preparation Example 2 to obtain 0.63 g of the compound (IXa) (yield: 58.9%).

Preparation Example 4

0.41 g of pyridine and 1.0 g of the compound (VIa) were added to 10 ml of ethanol, and hydrogen sulfide gas was bubbled therein with stirring at room temperature for 3.5 hours. Yellow solids which precipitated were filtered off and then treated in the same manner as in Preparation Example 1 to obtain 0.58 g of the compound (IXa) (Yield: 61.4%).

Also when triethylamine or triethanolamine was used in place of pyridine, the compound (IXa) was obtained.

EXAMPLE 6

Preparation of
2-methyl-3-hydroxy-4-(dimethylaminomethyleneamino)-5-thiocarbamoyl-pyrazole (VIIa) (Compound of the General Formula (VII) wherein $R^1$ and $R^2$ are both Methyl Group)

In Preparation Example 1 of Example 5, hydrogen sulfide gas was bubbled at room temperature for 5 hours. After it was confirmed by thin layer chromatography that the starting material (VIa) disappeared and only a new spot was formed, a part of the ethanol was distilled away at a low temperature. This new spot was isolated by fractionation thin layer chromatography and extracted with methanol. The methanol was distilled away to obtain the desired compound (VIIa) as a yellow oily material.

pmr Spectrum ($d_6$-DMSO) $\delta$ppm 2.73(3H, s), 2.90(3H, s), 3.32(3H, s), 7.95(1H, s).

MS(FD) (m/e); 227 (M+).

EXAMPLE 7

Preparation of
2-phenyl-3-hydroxy-4-nitroso-5-carbamoylpyrazole (IIIc) (Compound of the General Formula (III) wherein $R^1$ is a Phenyl Group)

The above compound was prepared from 2-phenyl-3-hydroxy-4-nitroso-5-ethoxycarbonyl-pyrazole (IIc) in the same manner as in Example 1.

Yield: 99%.

M.P.: 220°–222° C.

pmr Spectrum ($d_6$-DMSO) $\delta$ppm ; 7.29–7.93(m, 5H), 8.40, 8.63(br.s. ×2, 1H).

MS(m/e); 232(M+), 188(M+—$CONH_2$).

EXAMPLE 8

Preparation of
2-ethyl-3-hydroxy-7-mercapto-pyrazolo[4,3-d]pyrimidine (IXb) (Compound of the General Formula (IX) wherein $R^1$ is an Ethyl Group)

0.20 g of the above compound was prepared from 0.4 g of 2-ethyl-3-hydroxy-4-dimethylaminomethyleneamino-5-cyano-pyrazole (VIb) in the same manner as in Preparation Example 2 of Example 5 (yield: 52.9%).

M.P.: 275–279° C.

pmr Spectrum (d$_6$-DMSO) δppm; 1.35(t, 3H, J=7.2Hz), 4.11(q, 2H, J=7.2Hz), 7.76(s, 1H), 13.1(br.s., 1H).

MS(m/e); 196(M+), 168(M+—CH$_2$=CH$_2$).

EXAMPLE 9

Preparation of 2-phenyl-3-hydroxy-7-mercapto-pyrazolo[4,3-d]pyrimidine (IXc) (Compound of the General Formula (IX) wherein R$^1$ is a Phenyl Group)

The above compound was prepared directly from 2-phenyl-3-hydroxy-4-nitroso-5-carbamoyl-pyrazole (IIIc) in the same manner as in Preparation Example 3 of Example 5 with the exception that the stirring time at room temperature after the addition of phosphorus oxychloride was shortened from 14 hours to 1 hour.

0.88 g of the compound (IXc) was obtained from 1 g of the compound (IIIc) (yield: 78.6%)

M.P.: above 300° C.

pmr Spectrum (d$_6$-DMSO) δppm; 7.39–7.91(m, 6H). 13.67(br.s., 1H).

MS(m/e): 244(M+).

While the invention has been described in detail and with reference to specific embodiment thereof, it will be apparent to one skilled in the art that various changes and modifications can be made therein without departing from the spirit and scope thereof.

What is claimed is:

1. A pyrazole compound represented by the general formula (I):

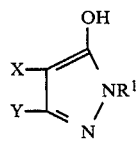

wherein:

R$^1$ is a hydrogen atom, an alkyl group having 1 to 4 carbon atoms, a phenyl group or a substituted phenyl group substituted with an alkyl group having 1 to 4 carbon atoms or an alkyloxy group having 1 to 4 carbon atoms;

X is a nitroso group, an amino group or (R$^2$)$_2$NCH=N— (wherein R$^2$ is an alkyl group having 1 to 3 carbon atoms); and Y is —C(O)NH$_2$ when R$^1$ is an alkyl group having 1 to 4 carbon atoms, a phenyl group or a substituted phenyl group and X is a nitroso group, or —C(O)NH$_2$ when R$^1$ is, an alkyl group having 1 to 4 carbon atoms, a phenyl group or a substituted phenyl group and X is an amino group, or CN or —C(S)NH$_2$ when R$^1$ is a hydrogen atom, an alkyl group having 1 to 4 carbon atoms, a phenyl group or a substituted phenyl group and X is (R$^2$)$_2$NCH=N—(wherein R$^2$ is the same as defined above).

2. The compound as claimed in claim 1 wherein R$^1$ is an alkyl group having 1 to 4 carbon atoms or a phenyl group, X is a nitroso group, an amino group or Me$_2$NCH=N—, and Y is CONH$_2$ when R$^1$ is an alkyl group having 1 to 4 carbon atoms or a phenyl group and X is a nitroso group, or CONH$_2$ when R$^1$ is an alkyl group having 1 to 4 carbon atoms or a phenyl group and X is an amino group, or CN or C(S)NH$_2$ when R$^1$ is an alkyl group having 1 to 4 carbon atoms or a phenyl group and X is Me$_2$NCH=N—.

3. The compound as claimed in claim 1 wherein R$^1$ is a methyl group, an ethyl group or a phenyl group, X is a nitroso group, an amino group or Me$_2$NCH=N—, and Y is CONH$_2$ when R$^1$ is a methyl group, an ethyl group or a phenyl group and X is a nitroso group, or CONH$_2$ when R$^1$ is a methyl group, an ethyl group or a phenyl group and X is an amino group, or CN or C(S)NH$_2$ when R$^1$ is a methyl group, an ethyl group or a phenyl group and X is Me$_2$NCH=N—.

4. The compound as claimed in claim 1 wherein R$^1$ is a methyl group, X is a nitroso group and Y is CONH$_2$.

5. The compound as claimed in claim 1 wherein R$^1$ is a methyl group, X is an amino group and Y is CONH$_2$.

6. The compound as claimed in claim 1 wherein R$^1$ is a methyl group, X is Me$_2$NCH=N- and Y is CN.

7. The compound as claimed in claim 1 wherein R$^1$ is a methyl group, X is Me$_2$NCH=N- and R is C(S)NH$_2$.

8. The compound as claimed in claim 1 wherein R$^1$ is an ethyl group, X is a nitroso group and Y is CONH$_2$.

9. The compound as claimed in claim 1 wherein R$^1$ is an ethyl group, X is an amino group and Y is CONH$_2$.

10. The compound as claimed in claim 1 wherein R$^1$ is an ethyl group, X is Me$_2$NCH=N—and Y is CN.

11. The compound as claimed in claim 1 wherein R$^1$ is a phenyl group, X is a nitroso group and Y is CONH$_2$.

12. The compound as claimed in claim 1 wherein R$^1$ is a phenyl group, X is an amino group and Y is CONH$_2$.

13. The compound as claimed in claim 1 wherein R$^1$ is a phenyl group, X is Me$_2$NCH=N—and Y is CN.

* * * * *